US009508256B2

(12) United States Patent
Brady-Kalnay et al.

(10) Patent No.: US 9,508,256 B2
(45) Date of Patent: Nov. 29, 2016

(54) MAGNETIC RESONANCE IMAGING (MRI) WITH DUAL AGENT CHARACTERIZATION

(71) Applicant: Case Western Reserve University, Cleveland, OH (US)

(72) Inventors: Susann Brady-Kalnay, Cleveland, OH (US); Vikas Gulani, Cleveland Heights, OH (US); Mark Griswold, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 625 days.

(21) Appl. No.: 14/068,537

(22) Filed: Oct. 31, 2013

(65) Prior Publication Data

US 2014/0292328 A1    Oct. 2, 2014

Related U.S. Application Data

(60) Provisional application No. 61/806,907, filed on Mar. 31, 2013.

(51) Int. Cl.
| | |
|---|---|
| A61K 49/06 | (2006.01) |
| G01R 33/48 | (2006.01) |
| G01R 33/56 | (2006.01) |
| G01R 33/563 | (2006.01) |
| G01R 33/58 | (2006.01) |
| A61B 5/055 | (2006.01) |
| G08C 23/06 | (2006.01) |
| G01R 33/36 | (2006.01) |
| A61B 5/00 | (2006.01) |

(52) U.S. Cl.
CPC ............. *G08C 23/06* (2013.01); *A61B 5/0017* (2013.01); *A61B 5/0073* (2013.01); *A61B 5/4244* (2013.01); *A61K 49/06* (2013.01); *G01R 33/3614* (2013.01); *G01R 33/3692* (2013.01); *G01R 33/4822* (2013.01); *G01R 33/56* (2013.01); *G01R 33/5608* (2013.01); *G01R 33/56366* (2013.01); *G01R 33/58* (2013.01); *A61B 5/055* (2013.01)

(58) Field of Classification Search
CPC .... A61B 5/0073; A61B 5/055; A61K 49/06; G01R 33/4822; G01R 33/5601; G01R 33/5608; G01R 33/56366; G01R 33/58
See application file for complete search history.

(56) References Cited

U.S. PATENT DOCUMENTS

| | | | |
|---|---|---|---|
| 7,319,784 B2 * | 1/2008 | Ryner | G06T 19/00 324/307 |
| 9,113,800 B2 * | 8/2015 | Schmidt | A61B 5/415 |
| 2008/0044358 A1 * | 2/2008 | Jacques | A61B 5/055 424/9.3 |
| 2010/0160173 A1 * | 6/2010 | Mchale | G01N 24/08 506/9 |

* cited by examiner

*Primary Examiner* — Gregory H Curran
(74) *Attorney, Agent, or Firm* — Quarles & Brady LLP

(57) ABSTRACT

Example apparatus and methods concern determining whether a target material appears in a region experiencing nuclear magnetic resonance. One method acquires a baseline value for a magnetic resonance parameter (MRP) while the region is not exposed to a molecular imaging agent that affects the MRP, acquiring a non-specific uptake value for the MRP while the sample is influenced by a non-specific molecular imaging agent and acquiring a specific uptake value for the MRP while the sample is influenced by a specific molecular imaging agent. The non-specific masking problem is solved by characterizing the region as a function of the baseline value, the non-specific uptake value, and the specific uptake value. The function relies on the similarities and differences between non-specific uptake of the non-specific molecular imaging agent, non-specific uptake of the specific molecular imaging agent, and specific uptake of the specific molecular imaging agent.

33 Claims, 13 Drawing Sheets

SEQUENCE LISTING

```
<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 1

Cys Gly Glu Gly Asp Asp Phe Asn Trp Glu Gln Val Asn Thr Leu Thr
1               5                   10                  15

Lys Pro Thr Ser Asp
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 2
```

```
Cys Gly Phe Thr Gln Pro Glu Thr Gly Thr Asp Asn Asp Leu Trp Ser
1               5                   10                  15
Val Asp Asn Glu Lys
            20
```

MAGNETIC RESONANCE IMAGING (MRI) WITH DUAL AGENT CHARACTERIZATION

PRIORITY CLAIM

This application claims the benefit of U.S. Provisional Patent Application 61/806,907 titled "Medical Imaging", filed Mar. 31, 2013.

BACKGROUND

Magnetic resonance imaging (MRI), nuclear magnetic resonance (NMR), and other magnetic resonance (MR) apparatus, systems, and approaches continue to become more sophisticated, powerful, precise, and complicated. MR involves the transmission of carefully controlled RF energy in the presence of carefully controlled magnetic fields to produce NMR in a material exposed to the RF energy.

Clinical MRI experiences constraints in spatial resolution due to hard physical and physiological limits. Increasing the strength of the magnetic fields used in MRI to, for example, 7T improves spatial resolution but at the expense of reduced contrast. As the magnetic field is strengthened, higher frequencies are needed for the RF to produce NMR because of the Larmor relationship:

$$\omega = \gamma B_0$$

where:
ω is the precession frequency
γ is the gyromagnetic ratio, and
$B_0$ is the magnetic field strength.

The higher frequencies used with the higher magnetic field strength apparatus yield reduced effectiveness of contrast agents used in MR. For example, a contrast agent that is used to produce a first change in T1 at a lower frequency and field strength may produce a second, lower change in T1 at a higher frequency and field strength. T1 refers to spin-lattice relaxation and T2 refers to spin-spin relaxation.

Due to the physical and physiological limits, conventional 1.5T or 3T human scanners have typically been limited to a resolution of approximately 2×2×2 mm³. However, some targets to be evaluated using MRI (e.g., cancer cells, tumors, proteins) may be significantly smaller than 2×2×2 mm³. For example, some tumor cells may be as small as 10 microns.

Conventionally, even though an MR signal may have been acquired from a tumor or cancer cell that was less than the voxel size used in MR acquisition and reconstruction, it has been difficult, if even possible at all, to distinguish voxels that include small targets (e.g., cancer cells) from voxels that do not include small targets due to the masking effect of non-specific uptake.

The non-specific uptake masking problem arises because conventional contrast agents have a large non-specific enhancement component. The non-specific enhancement issue arises even in specific targeted molecular imaging based contrast agents that only recognize (e.g., bind to) a specific marker. The non-specific enhancement may stem, for example, from vascular or other structural changes in tissue that cause non-specific uptake. The non-specific uptake masking issue is particularly problematic when attempting to image targets (e.g., tumors) smaller than a voxel.

FIGS. 1A and 1B show the baseline MR signal intensities SIG1 and SIG2 associated with two different voxels 110 and 120 that are experiencing NMR before a molecular imaging agent that affects an MR parameter (e.g., T1) has been applied. FIG. 1A illustrates a voxel 110 that includes a small tumor 100 while FIG. 1B illustrates a voxel 120 that is tumor free. Voxels 110 and 120 show a practically indistinguishable total MR signal intensity (e.g. SIG1 and SIG2 are equal).

FIGS. 1C and 1D show total MR signal intensities SIG3 and SIG4 associated with the two different voxels 110 and 120 experiencing NMR after a molecular imaging agent that affects an MR parameter has been applied. The molecular imaging agent may be, for example, a molecular imaging probe that recognizes tumor 100 and that will be taken up by tumor 100 more than it will be taken up by non-tumor tissue. The heavier shading in tumor 100 represents a higher concentration of the molecular imaging agent. The molecular imaging agent may be conjugated to a contrast agent (e.g., Gadolinium (Gd)). SIG3 is a function of baseline signal intensity (e.g., SIG1, SIG2) plus signal intensity due to non-specific uptake plus signal intensity due to specific uptake. SIG4 is a function of baseline signal intensity plus signal intensity due to non-specific uptake. Like SIG1 and SIG2 are difficult, if even possible to distinguish, so too SIG3 and SIG4 are practically indistinguishable. SIG3 and SIG4 are indistinguishable due, at least in part, to the dilution of the MR signal associated with specific uptake in tumor 100 by the MR signal associated with non-specific uptake throughout the voxel 110. Even though tumor 100 shows a large specific uptake of the molecular imaging agent, the signal associated with the specific uptake of the molecular imaging agent in tumor 100 is overwhelmed by the signal associated with non-specific uptake of the molecular imaging agent in the rest of the sample. The non-specific uptake in voxel 110 is so similar to the non-specific uptake in voxel 120, and the total MR signal is so dominated by the non-specific uptake, that MR signal due to specific uptake in tumor 100 is masked making SIG3 and SIG4 practically indistinguishable. Since SIG3 and SIG4 are indistinguishable, no specific characterization (e.g., diagnosis) of material in FIG. 1C (e.g., tumor 100) can be made, even though there was significant specific uptake in the tumor 100.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Figure 1A:
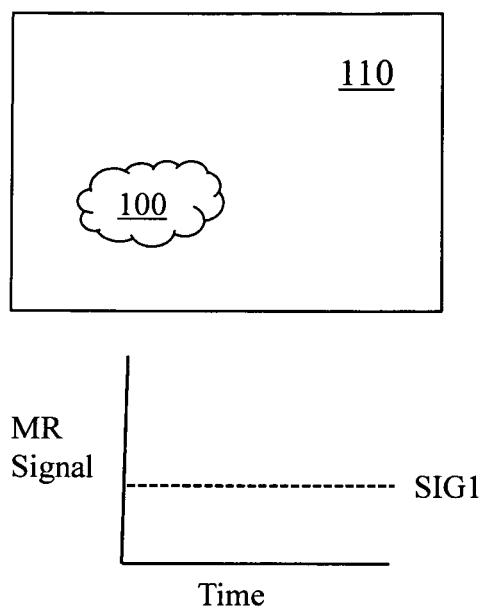
FIG. 1A illustrates MR signals associated with baseline, non-specific uptake, and specific uptake of a material (e.g., contrast agent) that impacts an MR parameter (e.g., T1)
Figure 1B:
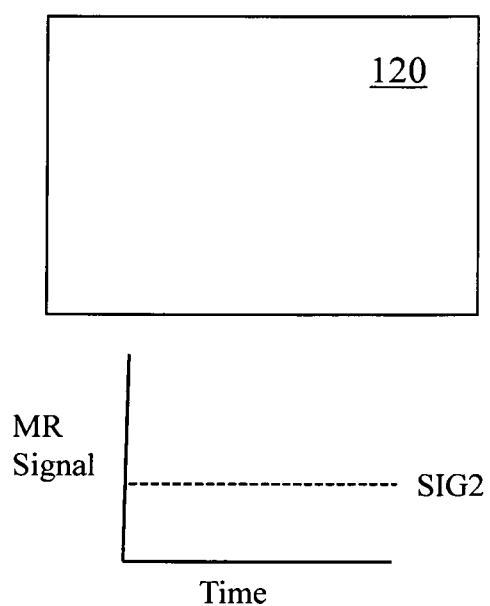
FIG. 1B illustrates MR signals associated with baseline, non-specific uptake, and specific uptake of a material that impacts an MR parameter.
Figure 1C:
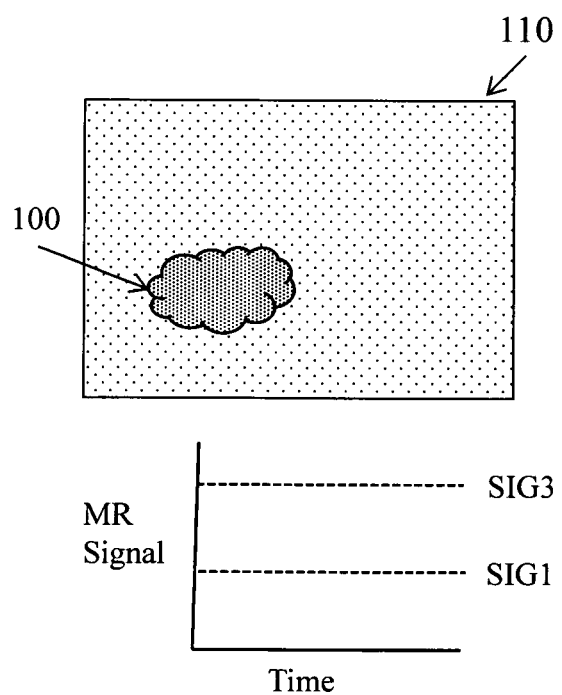
FIG. 1C illustrates MR signals associated with baseline, non-specific uptake, and specific uptake of a material that impacts an MR parameter and, FIG. 1D illustrates MR signals associated with baseline, non-specific uptake, and specific uptake of a material that impacts an MR parameter.
Figure 1D:
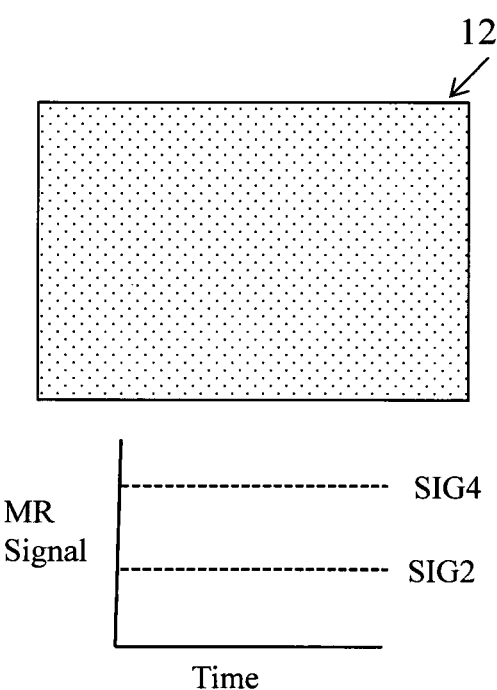

While the phenomenon of non-specific uptake produces the masking problem, the consistency of non-specific uptake between materials (e.g., molecular imaging agents) with similar molecular structure and content may also provide a solution to the non-specific masking problem. The solution may be available if two molecular imaging agents that exhibit similar non-specific uptake but exhibit different specific uptake can be employed in a controlled sequence in a relevant time frame. If the two molecular imaging agents include a material (e.g., contrast agent) that changes an MR parameter (e.g., T1) in a material exposed to the molecular imaging agents, and if the two molecular imaging agents can be employed in the same sample close enough in time in a controlled sequence, then the similar effects can be used to separate the different effects on the MR parameter. Separating the effects facilitates revealing the effect on an MR parameter due to specific uptake.

Consider two molecular imaging agents with differing sensitivities to recognizing fragments of a protein (e.g., protein tyrosine phosphatase mu (PTPμ)) associated with a certain type of cancer (e.g., glioblastoma) but with otherwise similar molecular forms. Because of their similar molecular forms, the two molecular imaging agents may produce similar to identical effects (e.g., enhancement) on an MR parameter (e.g., T1) due to non-specific uptake. Due to their differing sensitivities to recognizing a target (e.g., binding to the target in a protein:protein interaction), the two molecular imaging agents may produce different effects on the MR parameter due to specific uptake. For example, SBK2-Tris-(Gd-DOTA)$_3$ accumulates at about twice the concentration of scrambled-Tris-(Gd-DOTA)$_3$ in tumors containing the PTPμ fragment yet exhibits nearly identical non-specific uptake as scrambled-Tris-(Gd-DOTA)$_3$. SKB2-Tris-(Gd-DOTA)$_3$ and scrambled-Tris-(Gd-DOTA)$_3$ have identical molecular content even though their peptides have different orders of amino acids. The sequence of the peptide portion of scrambled-Tris-(Gd-DOTA)$_3$ may be a randomized or scrambled assembly of the SBK2 peptide. Therefore, if a baseline measurement of T1 is acquired before either molecular imaging agent is applied, if another measurement of T1 is made after the non-specific molecular imaging agent is applied, and if another measurement of T1 is made after the specific molecular imaging agent is applied, then the effect on T1 due to specific versus non-specific uptake may be understood and quantified and a specific characterization (e.g., diagnosis, phenotyping) of a material exposed to the molecular imaging agents may be made. For example, it may be possible to distinguish voxels that contain small amounts of a target material (e.g., tumor, protein, protein associated with tumor, biological material associated with pathology) from voxels that do not contain the target material.

As used herein, "SBK2" refers to a peptide that is described in: Burden-Gulley S M, Qutaish M Q, Sullivant K E, Tan M, Craig S E, Basilion J P, Lu Z R, Wilson D L, Brady-Kalnay S M. Single cell molecular recognition of migrating and invading tumor cells using a targeted fluorescent probe to receptor PTPmu. Int J Cancer. 2013 Apr. 1; 132(7):1624-32. doi: 10.1002/ijc.27838. Epub 2012 Oct. 11. PubMed PMID: 22987116; PubMed Central PMCID: PMC3558593, and in A Novel Molecular Diagnostic of Glioblastoma: Detection of an Extracellular Fragment of Protein Tyrosine Phosphatase μ, Brady-Kalnay et al., Neoplasia, Volume 12, Number 4, April 2010, pp 305-316; Molecular Magnetic Resonance Imaging of Tumors with a PTPμ Targeted Contrast Agent, Brady-Kalnay et al., Translational Oncology, 2013 June 1; 6(3): 329-37; and in United States Patent Application 2011/0171122, the contents of all of which are incorporated herein by reference.

In a dual agent approach, the two molecular imaging agents may produce different effects on the MR signal when a target is present in a sample. However, the different effect may be dominated by non-specific uptake. The effect on the MR signal due to non-specific uptake may be determined using the non-specific molecular imaging agent. Theoretically, the effect on the MR signal due to specific uptake may then be determined using the specific molecular imaging agent. Since the non-specific uptake is the same for the two agents and the specific uptake is different for the two molecular imaging agents, theoretically the two effects may then be separated to reveal a more precise MR signal that is due to just the specific uptake, thereby solving the masking problem. However, a practical result relies on quantitative relaxometry.

In one embodiment, the specific characterization may be made using a quantitative relaxometry approach. Recall that MR signal produced by a sample is a non-linear function of the underlying relaxation parameter T1. This non-linear function is not quantitative by itself. Recall also that when a contrast agent that affects T1 relaxation is present in a sample, that T1 is a non-linear function of the contrast agent concentration according to:

$$\frac{1}{T1\text{Observed}} = \frac{1}{T1\text{Initial}} + r1c \qquad \text{[Equation 1]}$$

where r1 is the relaxivity of the agent, and
c is the concentration of the agent.

The final observed T1 depends on both the initial T1 and the concentration of the agent. However, T1 alone with a single contrast agent is not adequate to specifically identify a sub-voxel sized target (e.g., tumor, protein) because of the non-specific uptake masking effect. T1 alone with a single contrast agent is not adequate even if the substance has a targeted specific uptake. For example, for two substances Sub1 and Sub2, where Sub1 exhibits non-specific uptake and Sub2 exhibits both non-specific and specific uptake, equals $$\frac{1}{T1ObservedSub1}$$

equals $$\frac{1}{T1ObservedSub2}$$

due to the masking issue when only one of the molecular imaging agents is used, regardless of whether the substance produces just non-specific uptake or both non-specific and specific uptake.

However, knowing that $$\frac{1}{T1ObservedSub1}$$

due to non-specific uptake equals $$\frac{1}{T1ObservedSub2}$$

due to non-specific uptake and that the $$\frac{1}{T1ObservedSub2}$$

due to specific uptake is different from $$\frac{1}{T1ObservedSub2}$$

due to non-specific uptake can be used to solve the masking problem when a sequenced dual-agent approach is employed.

The two different molecular imaging agents have similar to identical non-specific uptake and thus similar to identical effects on an MR signal or parameter when no target is present. But the two different molecular imaging agents have different specific uptake with respect to the target and thus different effects on an MR signal or parameter when the target is present. Therefore, sequentially exposing a sample to the two different molecular imaging agents within a certain time frame facilitates identifying whether a specific target (e.g., PTPμ) that the specific molecular imaging agent recognizes is present in a voxel in a sample. While PTPμ is described, other proteins, molecules, compounds, or targets may be similarly targeted and employed.

Figure 2:
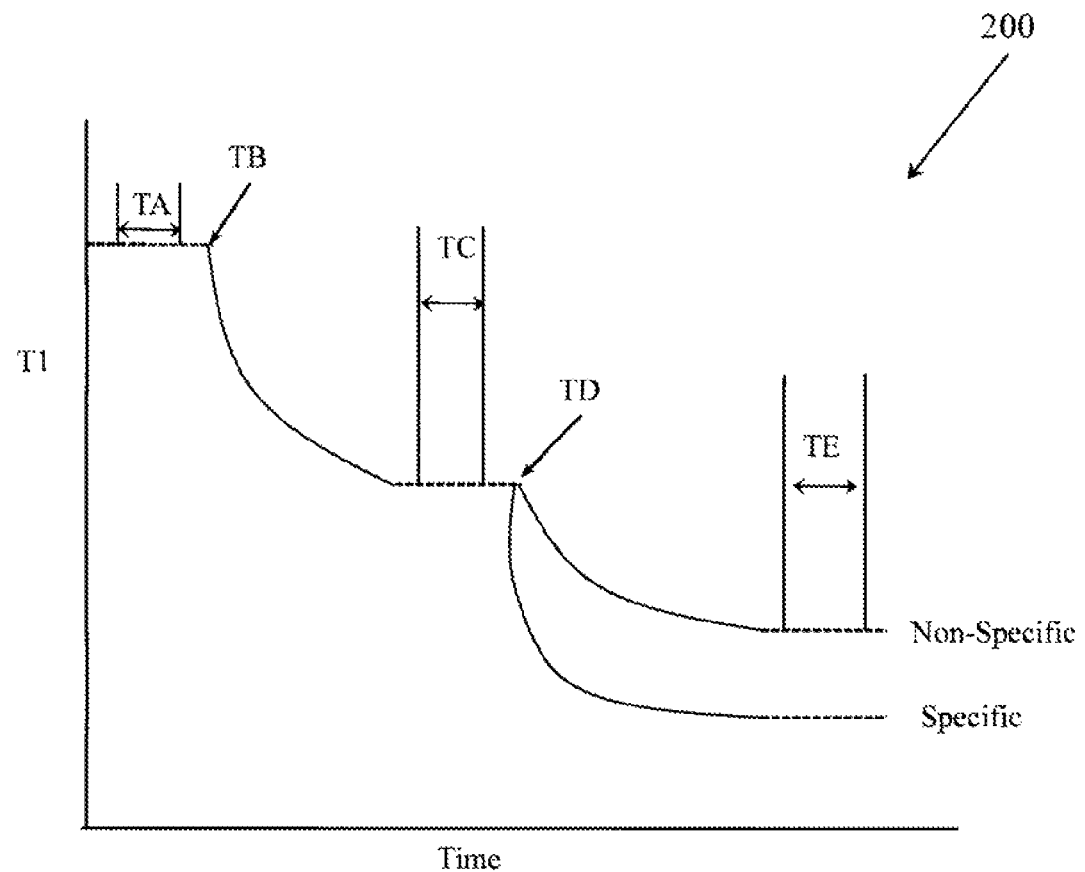
FIG. 2 illustrates a timeline of T1 measurements and molecular imaging agent introductions.

FIG. 2 illustrates a timeline associated with one embodiment of a sequential dual agent approach. The x axis of graph 200 represents time and the y axis represents T1 of a tissue experiencing NMR. During time interval TA an initial baseline T1 is measured for a region (e.g., voxel) in a sample. This baseline T1 represents the T1 relaxation of materials in the region without the presence of any T1 altering substances (e.g., contrast agents, Gd-containing molecules). At time TB, a non-specific molecular imaging agent whose non-specific uptake is similar to or identical to the non-specific uptake for a specific molecular imaging agent is presented to the sample. In one embodiment, the non-specific molecular imaging agent may be just a contrast agent (e.g., Gd-DOTA). During time interval TC, T1 is measured again and the change in T1 due to the non-specific molecular imaging agent is measured and analyzed. While the discrete value for T1 is interesting, the change in T1 between TA and TC may be more interesting because it can be quantified by converting the change to, for example, a map of the concentration (C1) of the non-specific molecular imaging agent. At time TD, a specific molecular imaging agent may be presented to the sample. The specific molecular imaging agent may be, for example, a molecular imaging agent that recognizes (e.g., binds to, is taken up by, accumulates in or near) the target. During time interval TE, T1 is measured again and the change in T1 due to the specific molecular imaging agent is measured and analyzed. The change in T1 between TC and TE may be quantified by, for example, converting the change to a map of the concentration (e.g., C2) due to both specific and non-specific uptake.

Note that the change in the MR signal and the change in observed T1 during both TC and TE may be different, even if the change in concentration remains the same due to the non-linear relationship between T1 and contrast agent concentration and the non-linear relationship between MR signal and T1. However, if there is an increased accumulation of the contrast agent due to specific or non-specific uptake, this will be evident as a difference in the quantified values. T1 may be analyzed using, for example, Drive Equilibrium Single Pulse Observation of T1 (DESPOT1) or Magnetic Resonance Fingerprinting (MRF). MRF is described in Magnetic Resonance Fingerprinting, Griswold et al., Nature 495, 187-192 (14 Mar. 2013) and in U.S. patent application Ser. No. 13/051,044, the contents of both of which are incorporated herein by reference.

Some portions of the detailed descriptions that follow are presented in terms of algorithms and symbolic representations of operations on data bits within a memory. These algorithmic descriptions and representations are used by those skilled in the art to convey the substance of their work to others. An algorithm is considered to be a sequence of operations that produce a result. The operations may include creating and manipulating physical quantities that may take the form of electronic values. Creating or manipulating a physical quantity in the form of an electronic value produces a concrete, tangible, useful, real-world result.

It has proven convenient at times, principally for reasons of common usage, to refer to these signals as bits, values, elements, symbols, characters, terms, numbers, and other terms. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, logic, processor, or similar electronic device that manipulates and transforms data represented as physical quantities (e.g., electronic values).

Example methods may be better appreciated with reference to flow diagrams. For simplicity, the illustrated methodologies are shown and described as a series of blocks. However, the methodologies may not be limited by the order of the blocks because, in some embodiments, the blocks may occur in different orders than shown and described. Moreover, fewer than all the illustrated blocks may be required to implement an example methodology. Blocks may be combined or separated into multiple components. Furthermore, additional or alternative methodologies can employ additional, not illustrated blocks.

Figure 3:
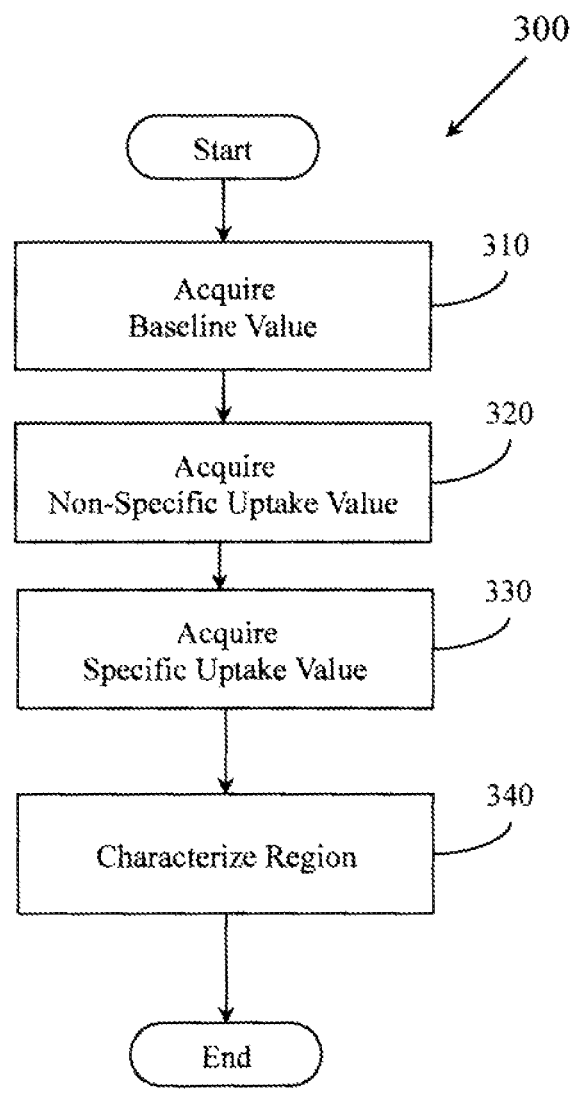
FIG. 3 illustrates a method associated with MRI with dual agent characterization.

FIG. 3 illustrates a method 300. Method 300 includes, at 310, acquiring a baseline value for a magnetic resonance (MR) parameter from a region in a sample while the sample is not exposed to a molecular imaging agent that affects the MR parameter in the sample. The MR parameter may be, for example, T1 relaxation, T2 relaxation, or some other magnetic resonance parameter. In one embodiment, the region is bounded by a voxel used in MRI reconstruction. Different region sizes may be employed. In one example, the voxel size is less than $2\times2\times2$ mm$^3$ while in another example the voxel size is greater than or equal to $2\times2\times2$ mm$^3$. Other sizes, including irregular sizes may be employed.

Method 300 also includes, at 320, acquiring a non-specific uptake value for the MR parameter while the sample is influenced by a non-specific molecular imaging agent. Even though the non-specific molecular imaging agent does not recognize a target material (e.g., tumor), the non-specific molecular imaging agent may affect the MR parameter due to non-specific uptake of the non-specific molecular imaging agent. The non-specific molecular imaging agent is configured to have similar to identical non-specific uptake as the specific molecular imaging agent. The sample may be, for example, a human tissue. Other tissue types (e.g., canine, bovine, equine, feline) and materials may be employed. The target material may be, for example, a protein, a chemical, a peptide, a cancer cell, a disease cell, a cancer marker, a disease marker, or other substance.

Method 300 also includes, at 330, acquiring a specific uptake value for the MR parameter while the sample is influenced by a specific molecular imaging agent that does recognize the target material. The specific molecular imaging agent may affect the MR parameter due to both non-specific uptake of the specific molecular imaging agent and due to specific uptake of the specific molecular imaging agent. In one example, the specific molecular imaging agent may be configured to have at least 50% more uptake in the target material than the general non-specific uptake in non-target material.

Method 300 also includes, at 340, characterizing the region. Characterizing the region may be a function of the baseline value, the non-specific uptake value, and the specific uptake value. For example, the effects due to non-specific uptake may be separated from the effects due to specific uptake. In one example, separating the effects may include subtracting one signal (e.g., concentration due to non-specific uptake) from another signal (e.g., concentration due to specific uptake). The different effects may be compared to the baseline or to each other and then a characterization may be made of whether the region includes a target material recognized by the specific molecular imaging agent. Since the method depends on the sample experiencing controlled NMR, the baseline value, the non-specific uptake value, and the specific uptake value are a function of magnetic resonance experienced in the sample as excited by an NMR apparatus. The NMR apparatus may employ different approaches including, but not limited to, DESPOT1, MRF, or other MR approaches. As described above in connection with the non-specific masking problem, the non-specific imaging agent and the specific imaging agent may produce indistinguishable or measurably different results under different conditions. For example, non-specific uptake of the non-specific molecular imaging agent (e.g., Scrambled) in an area that does not include the target material (e.g., tumor) and non-specific uptake of the specific molecular imaging agent (e.g., SBK2) in an area that does not include target material may not produce a measurably different effect on the MR parameter. Additionally, specific uptake of the specific molecular imaging agent (e.g., SBK2) in an area that includes the target material (e.g., tumor) and non-specific uptake of the non-specific molecular imaging agent (e.g., Scrambled) in an area that does include the target material produce a measurably different effect on the MR parameter in the region. Furthermore, specific uptake of the specific molecular imaging agent (e.g., SBK2) in an area that includes the target material (e.g., tumor) and non-specific uptake of the specific molecular imaging agent (e.g., SBK2) in an area that does not include the target material produce a measurably different effect on the MR parameter in the region.

These measurably different effects and indistinguishable effects facilitate separating the effects of the non-specific molecular imaging agent and the specific molecular imaging agent which in turn facilitate determining whether there was sufficient specific uptake of the specific molecular imaging agent to facilitate making a characterization (e.g., diagnosis). In one example, separating the effects may include subtracting one signal (e.g., concentration due to non-specific uptake) from another signal (e.g., concentration due to specific uptake). Recall that non-specific uptake of the non-specific probe may be higher in an area that includes tumor cells due to enhanced permeability and retention (EPR).

Different molecular imaging agents may be employed. In one example, the specific molecular imaging agent is a first peptide conjugated to a contrast agent. The first peptide may be, for example, SBK2. In one example, the non-specific molecular imaging agent is just a contrast agent or a material that changes T1 in the sample (e.g., Gadolinium). In another example, the non-specific molecular imaging agent is a second peptide conjugated to the contrast agent (e.g., Gadolinium). As described above, in one example, to facilitate having the non-specific molecular imaging agent and the specific molecular imaging agent exhibit similar to identical non-specific uptake, the second peptide may be a randomized version of the first peptide or a scrambled version of the first peptide. While Gadolinium is described, other contrast agents, including but not limited to magnetic nanoparticles may be employed.

The specific molecular imaging agent may be configured or chosen to facilitate identifying a specific target. Different targets may be sought. In one example, the target material is a protein associated with a disease. In one example, the target material is a PTPµ fragment associated with cancer (e.g., glioblastoma multiforme). When the target material is a protein, the specific molecular imaging agent may recognize the target material by binding to the target material in a protein:protein interaction. Other mechanisms for recognition that lead to increased concentration of the contrast agent in or near the target material may also be involved.

The non-specific uptake value is a function of the concentration of the non-specific molecular imaging agent in the region. Similarly, the specific uptake value is a function of the concentration of the specific molecular imaging agent in the region. Since the values represent concentrations, in one example the changes in T1 may be quantified by converting the values to concentration maps.

Method 300 and other methods and apparatus described herein may be more sensitive than conventional systems, in some cases up to two orders of magnitude more sensitive than conventional systems. For example, method 300 and other methods and apparatus described herein may be able to detect a tumor that is less than 1% the size of the region, less than 5% the size of the region, less than 10% of the size of the region, less than 50% the size of the region, or other sizes. In another example, method 300 and other methods and apparatus described herein may be able to detect a change in concentration of less than 250 nM of the contrast agent in the region, of less than 500 nM of the contrast agent in the region, of less than 1000 nM of the contrast agent, or other changes of concentration.

Figure 4:
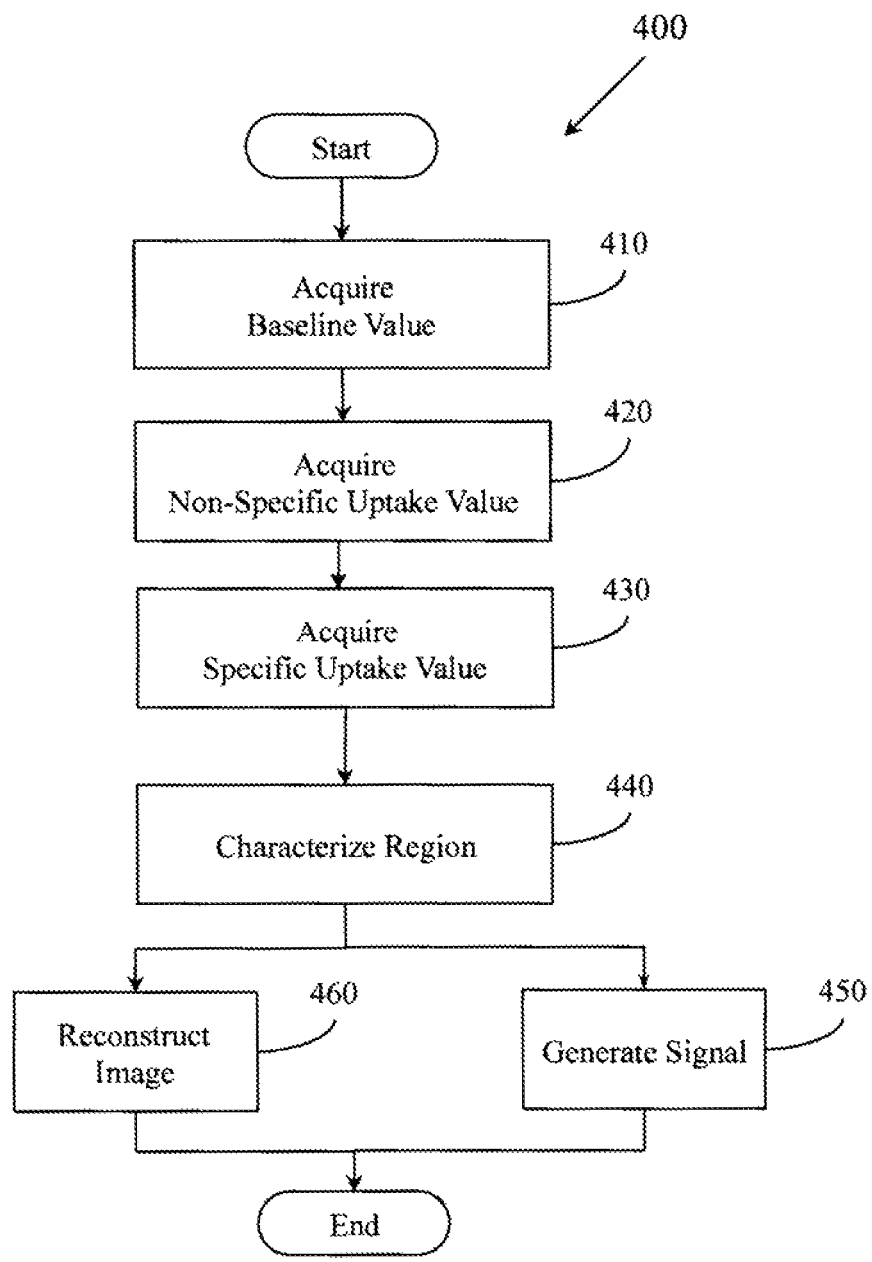
FIG. 4 illustrates a method associated with MRI with dual agent characterization.

FIG. 4 illustrates a method 400. Method 400 includes some actions similar to those described in connection with method 300. For example, method 400 includes acquiring a baseline value at 410, acquiring a non-specific uptake value at 420, acquiring a specific uptake value at 430, and characterizing a region at 440. However method 400 includes additional actions.

Method 400 also includes, at 460, reconstructing a magnetic resonance image from magnetic resonance signals received from the sample. The magnetic resonance image may include information that is a function of the baseline value, the non-specific uptake value, or the specific uptake value. The image may include information concerning the target material (e.g., tumor). Since the example methods and apparatus described herein are more sensitive than conventional systems, the reconstructed image may be more useful for diagnosing pathology.

Method 400 also includes, at 450, controlling a signal detection apparatus to generate a signal that indicates that the target material is present in the sample. In one embodiment, the signal may identify a phenotype of the target material. The signal may also indicate other properties of the sample, target material, or region. For example, the signal may indicate that the target material is present in the region. In one embodiment, the signal may be used to control additional processing for the region. For example, if the signal indicates that the target material is present in a region, then additional imaging or different types of imaging may be employed for the region. Other actions may be taken. The signal may be, for example, a visual signal, an audible signal, an electrical signal, a computer interrupt, a procedure call, a voltage on a line, a frequency on a line, or other signal.

In one embodiment, method 400 may both reconstruct an image at 460 and generate a signal at 450. In other embodiments, method 400 may either generate a signal at 450 or reconstruct an image at 460.

Figure 5:
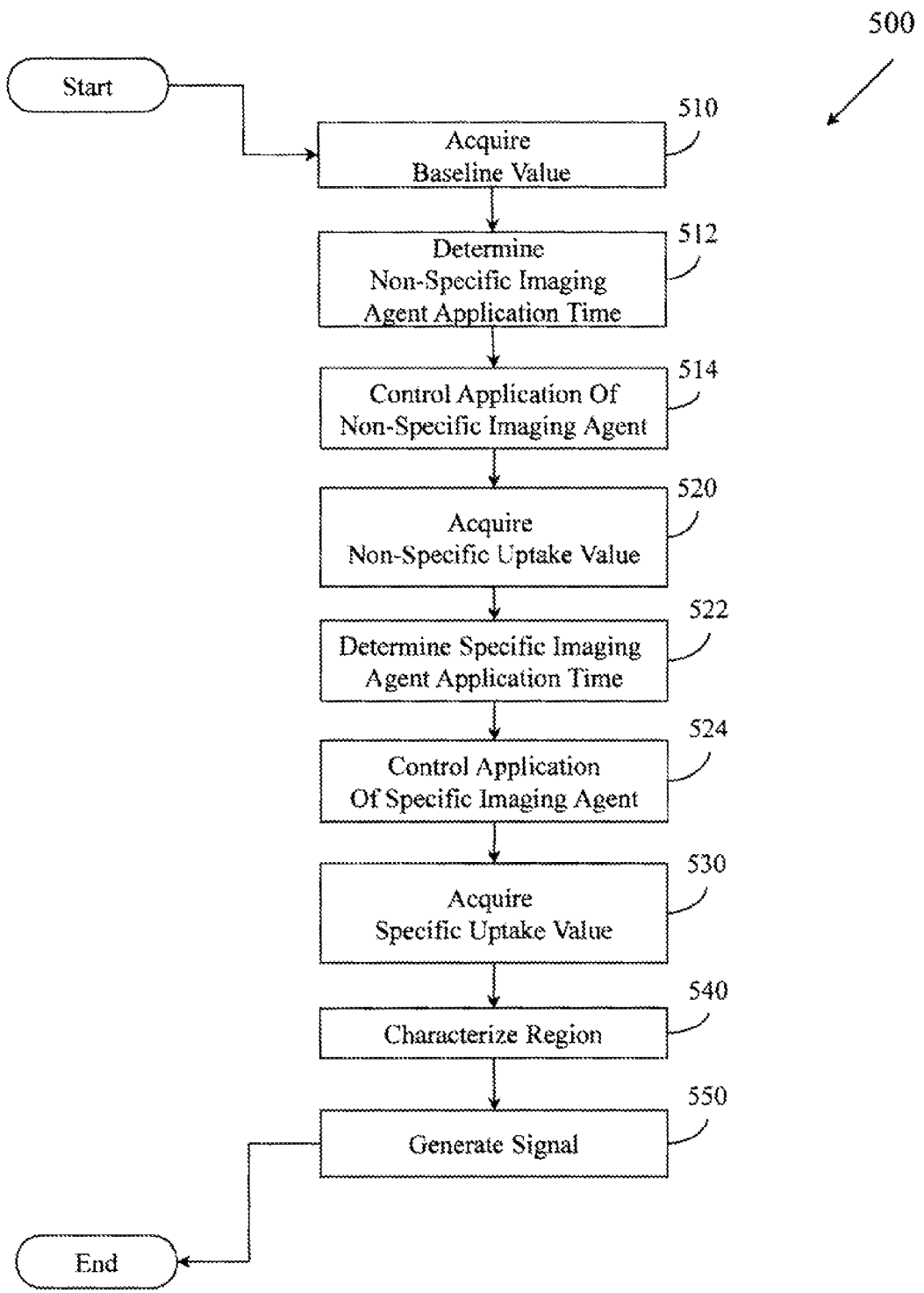
FIG. 5 illustrates a method associated with MRI with dual agent characterization.

FIG. 5 illustrates a method 500. Method 500 includes some actions similar to those described in connection with method 400. For example, method 500 includes acquiring a baseline value at 510, acquiring a non-specific uptake value at 520, acquiring a specific uptake value at 530, characterizing a region at 540, and generating a signal at 550. However method 500 includes additional actions. The additional actions concern coordinating the application of the molecular imaging agents and controlling when T1 measurements or other measurements are made.

In different embodiments, different sequences or series of measurements may be made. The timing and sequence of the measurements may be determined, at least in part, by the timing and sequence with which the molecular imaging agents are presented. In one example, the baseline value is acquired before both the non-specific uptake value and the specific uptake value. In another example, the baseline value could be acquired after one or more of the molecular imaging agents had been determined to have cleared the sample. In one embodiment, the non-specific uptake value is acquired before the specific uptake value. In another embodiment, the specific uptake value is acquired before the non-specific uptake value.

In one embodiment, the non-specific uptake value may be acquired after the non-specific molecular imaging agent has been applied to the sample and an effect on the MR parameter associated with the non-specific molecular imaging agent has reached a first threshold level. The first threshold level may be, for example, a change in T1 of 10%, 25%, 50%, or some other amount. The first threshold level may also be, for example, a decrease of T1 for at least thirty seconds, for at least sixty seconds, for at least ninety seconds, or for some other period of time. The first threshold level may also be, for example, a maximum observed change of T1 in a time period.

In one embodiment, the specific uptake value may be acquired after an effect on the MR parameter associated with the non-specific molecular imaging agent has recrossed the first threshold level. Thus, a known or maximum effect on T1 due to the non-specific molecular imaging agent will have been measured before the specific molecular imaging agent is applied. The specific uptake value will be acquired after the specific molecular imaging agent has been applied, and, in one embodiment, may be measured after an effect on the MR parameter associated with the specific molecular imaging agent has reached a second threshold level. The second threshold level may be, for example, a change in T1 of 10%, 25%, 50%, or some other amount. The second threshold level may also be, for example, a change of T1 for at least thirty seconds, for at least sixty seconds, for at least ninety seconds, or for some other period of time. The second threshold level may also be, for example, a maximum change of T1 in a time period. While the example describes acquiring data concerning specific uptake after acquiring data concerning non-specific uptake, other data acquisition orders may be employed.

Thus, method 500 includes, at 512, determining when the non-specific molecular imaging agent should be applied and, at 514, controlling application of the non-specific molecular imaging agent based on the determination at 512. At 520, the non-specific uptake value is acquired. Method 500 may determine when to acquire the non-specific uptake value as a function of when the non-specific molecular imaging agent was applied, as a function of the observed effect of the application of the non-specific molecular imaging agent, or based on other factors. Controlling application of the non-specific molecular imaging agent may include, for example, controlling an intravenous delivery device, controlling a nano-particle release mechanism, providing a signal to a doctor, nurse, or technician, or other action.

Method 500 also includes, at 522, determining when the specific molecular imaging agent should be applied and, at 524, controlling application of the specific molecular imaging agent. Controlling application of the specific molecular imaging agent may include, for example, controlling an intravenous delivery device, controlling a nano-particle release mechanism, providing a signal to a doctor, nurse, or technician, or other action. Method 500 may determine when to acquire the specific uptake value as a function of when the non-specific molecular imaging agent was applied, as a function of the observed effect of the application of the non-specific molecular imaging agent, as a function of when the specific molecular imaging agent was applied, as a function of the observed effect of the application of the specific molecular imaging agent, or as a function of other data. While applying the non-specific molecular imaging agent first, followed by applying the specific molecular imaging agent has been described, imaging agents may be applied in other orders.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and other entities. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

Figure 6:
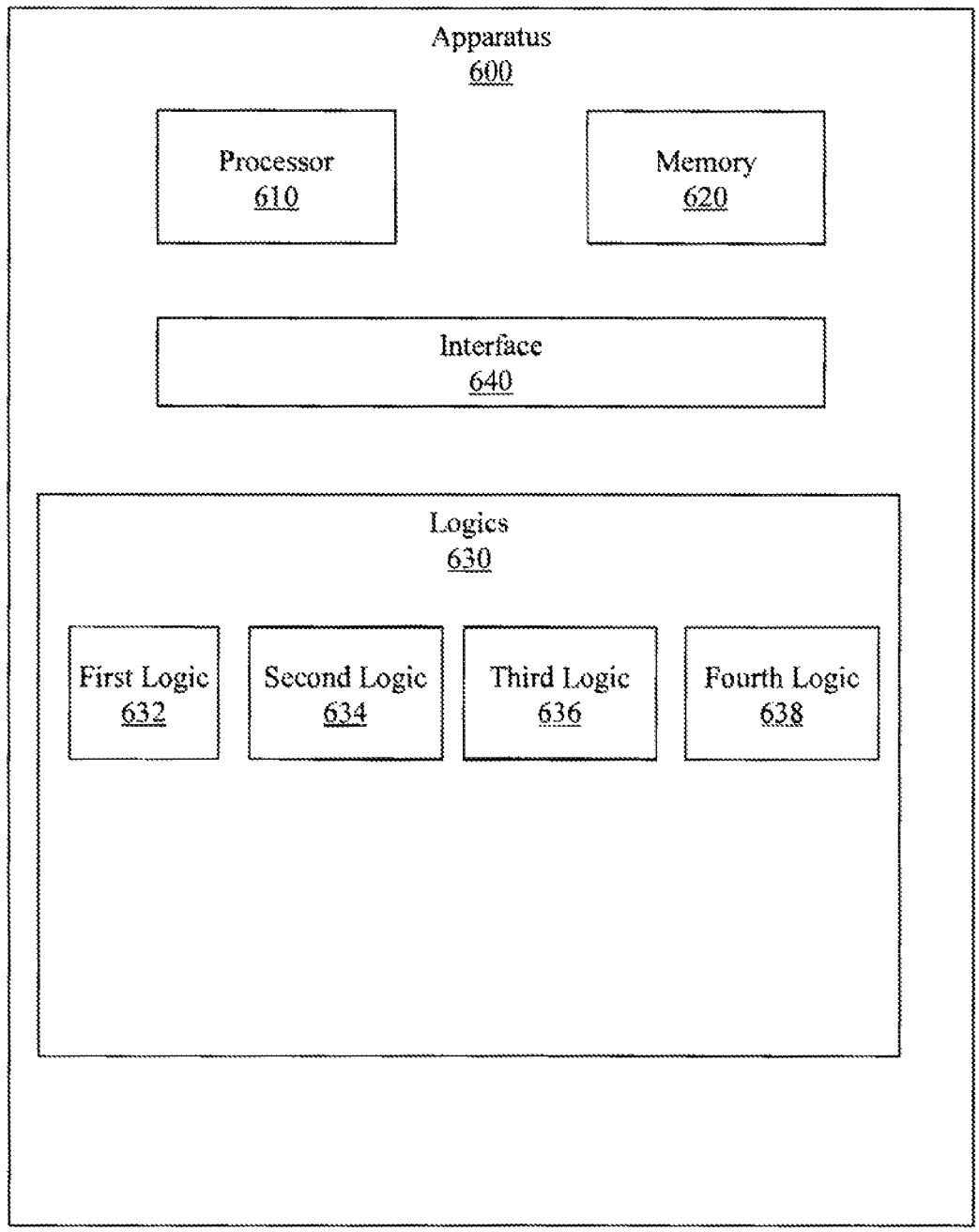
FIG. 6 illustrates an apparatus associated with MRI with dual agent characterization.

FIG. 6 illustrates an apparatus 600 configured for use with a magnetic resonance (MR) apparatus. Apparatus 600 includes a processor 610, a memory 620, a set of logics 630, and an interface 640 to connect the processor 610, the memory 620, and the set of logics 630.

The set of logics 630 includes a first logic 632 that is configured to measure a baseline T1 in a sample when no T1 altering molecular imaging agent is present in the sample. The first logic 632 may measure the baseline T1 from MR signals received from the sample after the sample was excited by an MR apparatus.

The set of logics 630 also includes a second logic 634 that is configured to measure a change in T1 in the sample from the baseline T1 due to the presence of a non-specific molecular imaging agent in the sample. The non-specific molecular imaging agent will include a contrast agent and thus the change in T1 will be due to a change of concentration of the contrast agent in the sample. In one example, T1 or the change in T1 may be quantified by converting the values to a concentration.

The set of logics 630 also includes a third logic 636 that is configured to measure a change in T1 in the sample from the baseline T1 due to the presence of a specific molecular imaging agent in the sample. While a change in T1 from the baseline T1 is described, in one embodiment, the change in T1 from the measurements taken after the effect of the non-specific molecular imaging agent are observed may be measured. The specific molecular imaging agent will also include a contrast agent and thus the change in T1 will be due to a change of concentration of the contrast agent in the sample. In one example, T1 or the change in T1 may be quantified by converting the values to a concentration.

The set of logics 630 also includes a fourth logic 638 that is configured to generate a signal identifying whether a target material is present in the sample. In one embodiment, fourth logic 638 identifies whether the target material is present as a function of the baseline T1, the change in T1 due to the non-specific molecular imaging agent, and the change in T1 due to the specific molecular imaging agent. For the fourth logic 638 to be able to identify whether the target material is present, there need to be certain relationships between non-specific uptake for the non-specific molecular imaging agent and the specific molecular imaging agent. Additionally, there need to be certain relationships between non-specific uptake of the specific molecular imaging agent and specific uptake of the specific molecular imaging agent. For example, the molecular imaging agents need to be selected and applied so that non-specific uptake of the non-specific molecular imaging agent and non-specific uptake of the specific molecular imaging agent do not produce a measurably different effect on T1. Additionally, the molecular imaging agents need to be selected and applied so that specific uptake of the specific molecular imaging agent and non-specific uptake of the specific molecular imaging agent produce a measurably different effect on T1, and so that specific uptake of the specific molecular imaging agent and non-specific uptake of the non-specific molecular imaging agent produce a measurably different effect on T1.

In one embodiment, the specific molecular imaging agent is SBK2 conjugated to Tris-(Gd-DOTA)$_3$ and the non-specific molecular imaging agent is a scrambled or randomized version of the peptide SBK2 conjugated to Tris-(Gd-DOTA)$_3$. Other specific molecular imaging agents and non-specific molecular imaging agents may have different peptides or polypeptides conjugated to different contrast agents (e.g., magnetic nanoparticles).

Apparatus 600 is much more sensitive than conventional apparatus that have not solved the non-specific masking problem. In one embodiment, the fourth logic 638 is configured to generate the signal upon determining that the target material occupies less than fifty % of the voxel, less than 25% of the voxel, less than 10% of the voxel, less than 1% of the voxel, or under other conditions. In other embodiments, the fourth logic 638 may be configured to generate the signal upon determining a change in concentration of the contrast agent of at least 1000 nM, of at least 500 nM, or of at least 250 nM. Other changes in concentrations may be employed in other examples. The signal may be, for example, a visual signal, an audible signal, an electrical signal, a computer interrupt, a procedure call, a voltage on a line, a frequency on a line, or other signal.

Processor 610 may be, for example, a signal processor, a microprocessor, an application specific integrated circuit (ASIC), or other control and processing logic circuitry for performing tasks including signal coding, data processing, input/output processing, power control, or other functions. Memory 620 can include non-removable memory or removable memory. Non-removable memory may include random access memory (RAM), read only memory (ROM), flash memory, a hard disk, or other memory storage technologies. Removable memory may include flash memory, or other memory storage technologies, such as "smart cards." Memory 620 may be configured to store the baseline value, the non-specific uptake value, the specific uptake value, or other information.

In one embodiment, the apparatus 600 may be a general purpose computer that has been transformed into a special purpose computer through the inclusion of the set of logics 630. The set of logics 630 may be configured to perform input and output. Apparatus 600 may interact with other apparatus, processes, and services through, for example, a computer network. Elements of the apparatus 600 may be configured to communicate with each other, but not all connections have been shown for clarity of illustration.

Figure 7:
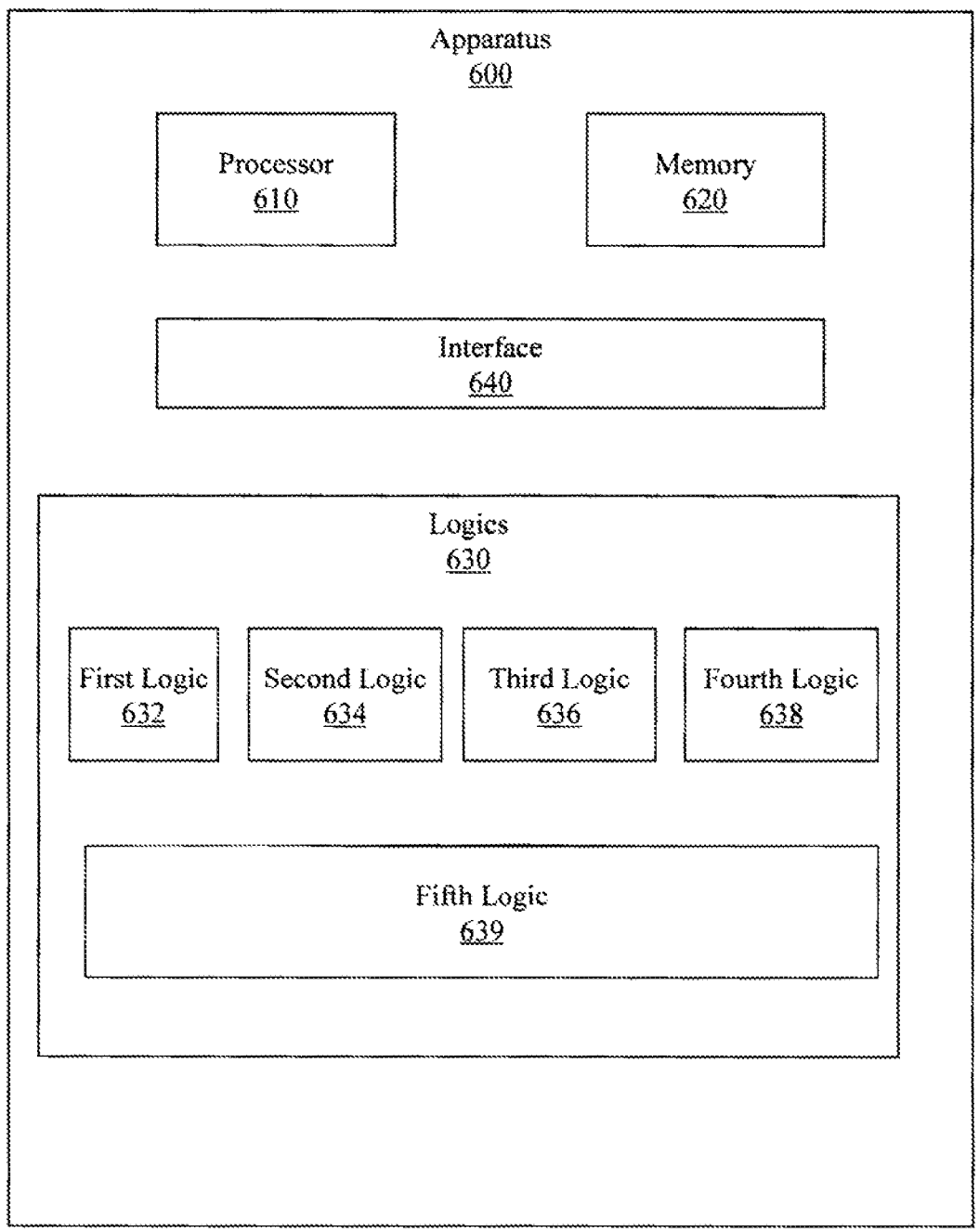
FIG. 7 illustrates an apparatus associated with MRI with dual agent characterization.

FIG. 7 illustrates another embodiment of apparatus 600 (FIG. 6). This embodiment of apparatus 600 includes a fifth logic 639 that is configured to control when the non-specific molecular imaging agent is applied to the sample and to control when the specific molecular imaging agent is applied to the sample. Controlling the order in which molecular imaging agents are presented to the sample and controlling when measurements are taken facilitates separating the effects of specific uptake, if any, from non-specific uptake. The fifth logic 639 may determine a time for measuring the baseline T1. The time may include a start time, an end time, a duration, or other information for controlling when the baseline T1 will be measured. Since T1 values are not quantitative by themselves, acquiring the baseline value facilitates quantifying relative values.

Fifth logic 639 is also configured to determine a time for introducing the non-specific molecular imaging agent into the sample. In one embodiment, the time for introducing the non-specific molecular imaging agent may be used to control a medical device (e.g., intravenous drip system, intravenous injection system) to introduce the non-specific molecular imaging agent into the sample. When the non-specific molecular imaging agent is delivered through the blood stream, there may be a delay between introduction and any observable effect, a consistent observable effect, a peak observed effect, or a reduction and then ending of the observed effect. Therefore, fifth logic 639 is configured to determine a time for measuring the change in T1 due to the non-specific molecular imaging agent. The time may be a function of when the first effect is observed, when the effect becomes consistent, when the effect exceeds a threshold (e.g., 10% relaxation change), or other factors.

Fifth logic 639 is also configured to determine a time for introducing the specific molecular imaging agent into the sample. In one embodiment, the time for introducing the specific molecular imaging agent may be used to control a medical device (e.g., intravenous drip system, intravenous injection system) to introduce the specific molecular imaging agent into the sample. When the specific molecular imaging agent is delivered through the blood stream, there may be a delay between introduction and any observable effect, a consistent observable effect, a peak observed effect, and a reduction and then ending of the observed effect. Therefore, fifth logic 639 is configured to determine a time for measuring the change in T1 due to the specific molecular imaging agent. The time may be a function of when the effect is observed, when the effect becomes consistent, when the effect exceeds a threshold (e.g., 10% relaxation change), or other factors. In one example, the time may also be a function of when an observed effect associated with the non-specific molecular imaging agent has fallen below a threshold.

Figure 8:
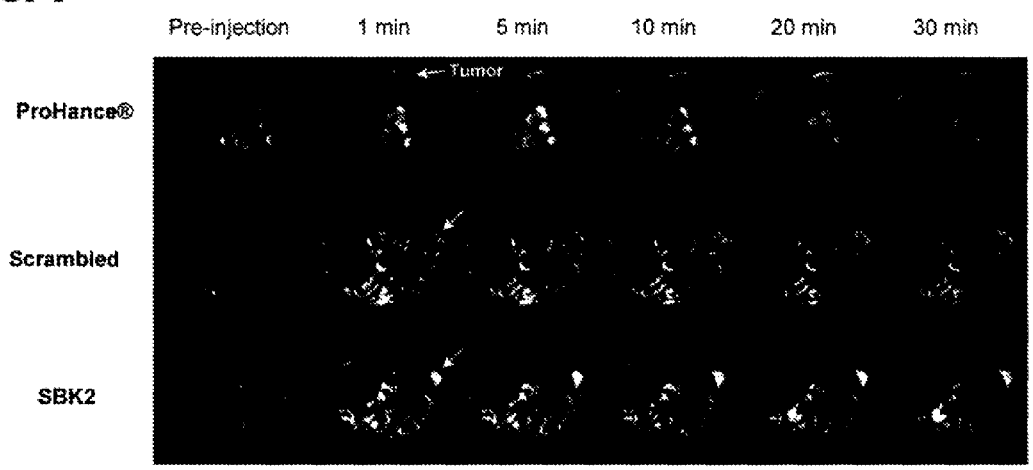
FIGS. 8A and 8B illustrate that the SBK2 targeted contrast agent improves the enhancement of LN-229 tumors.
Figure 8:
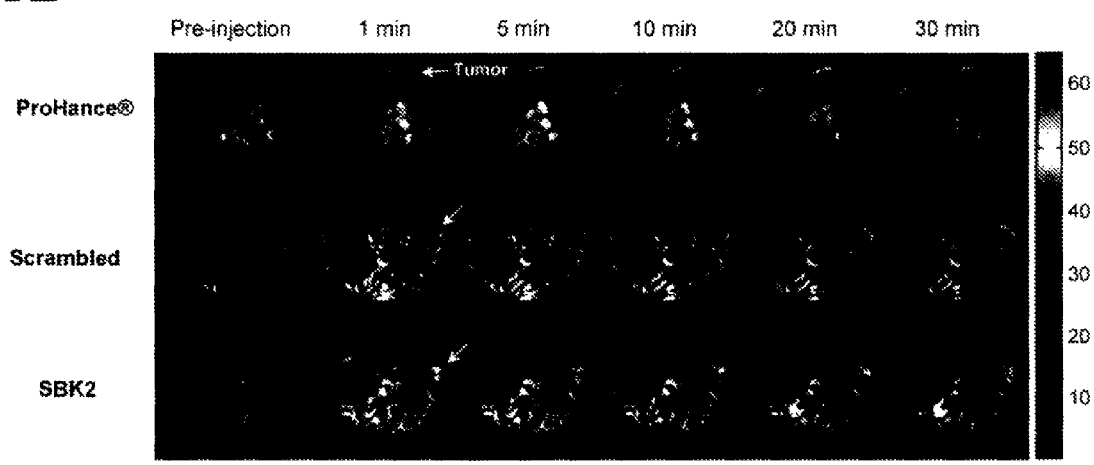

FIGS. 8A and 8B illustrate that the SBK2 based specific molecular imaging agent improves the enhancement of LN-229 tumors. FIG. 8A illustrates representative T1-weighted axial 2D gradient images of LN-229 flank tumor-bearing mice before (pre-injection) and at 1, 5, 10, 20, and 30 minutes after the intravenous injection of ProHance, scrambled Tris-(Gd-DOTA)$_3$, or SBK2-Tris-(Gd-DOTA)$_3$ at 0.1 mmol Gd/kg [n=7 tumors from four mice for ProHance; n=11 tumors from six mice for both SBK2-Tris-(Gd-DOTA)$_3$ and SBK2-Tris-(Gd-DOTA)$_3$]. FIG. 8B illustrates Axial 2D gradient images shown in FIG. 8A with heat map overlays on the tumor to indicate contrast intensity.

The SBK2 based specific molecular imaging agent was developed as a diagnostic imaging tool. To function as an imaging tool, SBK2 was conjugated to a gadolinium chelate [SBK2-Tris-(Gd-DOTA)$_3$] to generate an MR-detectable molecular imaging agent. The ability of SBK2-Tris-(Gd-DOTA)$_3$ to function as a contrast agent was compared to a macrocyclic gadolinium chelate (Gadoteridol, ProHance) and to a scrambled molecular imaging agent linked to gadolinium [scrambled Tris-(Gd-DOTA)$_3$]. SBK2-Tris-(Gd-DOTA)$_3$ labeled human glioma tumors with a high level of contrast persisting for 2 hours. The contrast enhancement of SBK2-Tris-(Gd-DOTA)$_3$ was significantly higher than that observed with ProHance alone. SBK2-Tris-(Gd-DOTA)$_3$ labeling of PTPµ extracellular fragment retained in the tumor microenvironment is a more specific MR molecular imaging agent than a nonspecific gadolinium chelate.

The SBK2 peptide was conjugated to Gd-DOTA using an increased molar ratio of Gd-DOTA monoamide to peptide to generate an MR-visible molecular imaging agent [SBK2-Tris-(Gd-DOTA)$_3$]. A scrambled version of the SBK2 peptide was also conjugated to Gd-DOTA to generate a non-targeted control agent [scrambled Tris-(Gd-DOTA)$_3$]. The SBK2 peptide with an N-terminal cysteine (C-GEGDDFN-WEQVNTLTKPTSD) was synthesized using standard solid-phase peptide synthesis. Matrix-assisted laser desorption/ionization time-of-flight (MALDI-TOF; Autoflex Speed, Bruker) mass spectra (m/z, M$^+$) were given as follows: 2355.52 (observed) and 2355.00 (calculated). Scrambled peptide (C-GFTQPETGTDNDLWSVDNEK) was synthesized by the same method [MALDI-TOF (m/z, M$^+$): 2355.56 (observed); 2355.00 (calculated)]. SBK2 was conjugated to maleimido-Tris-propargyl, then subsequently to azido-(Gd-DOTA). The reaction was traced by MALDI-TOF until Gd-DOTA was fully attached [MALDI-TOF (m/z, M$^+$): 4664.87 (observed); 4664.62 (calculated); Inductively coupled plasma optical emission spectroscopy (ICP-OES) analysis for Gd$^{3+}$ content: 9.56% (observed); 10.1% (calculated)]. Scrambled Tris-(Gd-DOTA)$_3$ was synthesized by the same method with a yield of 68% [MALDI-TOF (m/z, M$^+$): 4664.75 (observed); 4664.62 (calculated); ICP (Gd$^{3+}$ content): 9.68% (observed); 10.1% (calculated)].

Figure 9:
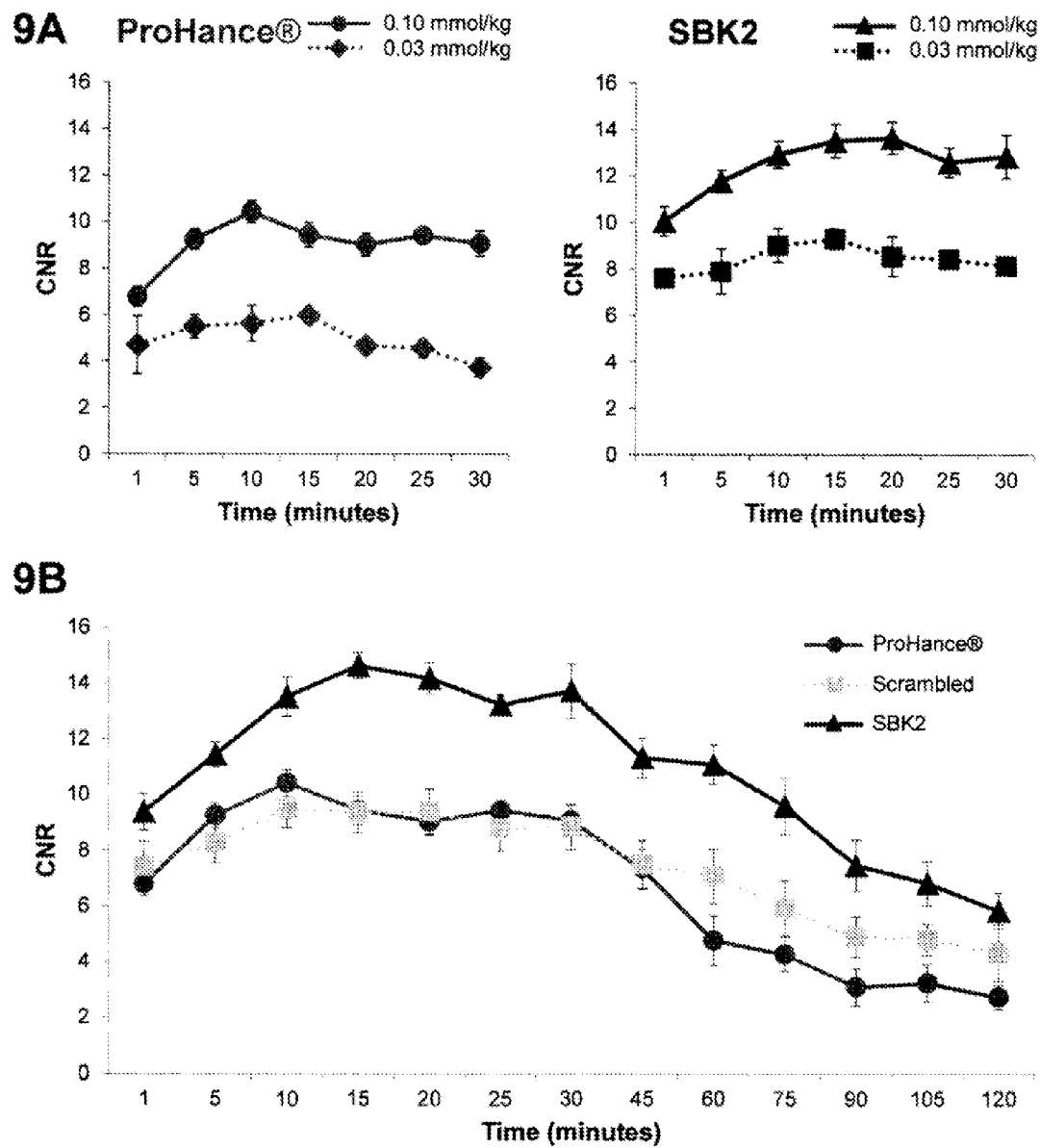
FIG. 9A illustrates quantitation of LN-229 flank tumor enhancement following administration of control or targeted contrast agents.
FIG. 9B illustrates a comparison of LN-229 flank tumor contrast to noise ratio (CNR) over a 2-hour period following intravenous administration of ProHance, scrambled Tris-(Gd-DOTA)$_3$, or SBK2-Tris-(Gd-DOTA)$_3$ contrast agents.

FIG. 9A illustrates quantitation of LN-229 flank tumor enhancement following administration of control or targeted contrast agents in xenograft mice. FIG. 9A illustrates dose-response plots of LN-229 flank tumor contrast to noise ratio (CNR) with ProHance or SBK2-Tris-(Gd-DOTA)$_3$ administered at 0.03 mmol Gd/kg (n=3 per condition) or 0.1 mmol Gd/kg [n=7 tumors from four mice for ProHance; n=11 tumors from six mice for SBK2-Tris-(Gd-DOTA)$_3$].

FIG. 9B illustrates a comparison of LN-229 flank tumor CNR over a 2-hour period following intravenous administration of ProHance, scrambled Tris-(Gd-DOTA)$_3$, or SBK2-Tris-(Gd-DOTA)$_3$ contrast agents (0.1 mmol Gd/kg; n=6 tumors from three mice per condition). Data is shown as means±SEM. The targeted agent SBK2-Tris-(Gd-DOTA)$_3$ showed improved tumor CNR when compared with the nontargeted scrambled Tris-(Gd-DOTA)$_3$ or ProHance. SBK2-Tris-(Gd-DOTA)$_3$ resulted in an approximate 55% increase in tumor CNR over scrambled Tris-(Gd-DOTA)$_3$ or ProHance at 15 to 45 minutes post-injection (P<0.001). At 60 to 120 minutes post-injection, the ProHance cleared more rapidly than SBK2-Tris-(Gd-DOTA)$_3$ resulting in greater than 110% increase in SBK2-Tris-(Gd-DOTA)$_3$ tumor CNR compared with ProHance (P<0.001). The SBK2-Tris-(Gd-DOTA)$_3$ tumor CNR was approximately 53% greater than the scrambled Tris-(Gd-DOTA)$_3$ tumor CNR at 60 to 90 minutes (P<0.001).

Figure 10:
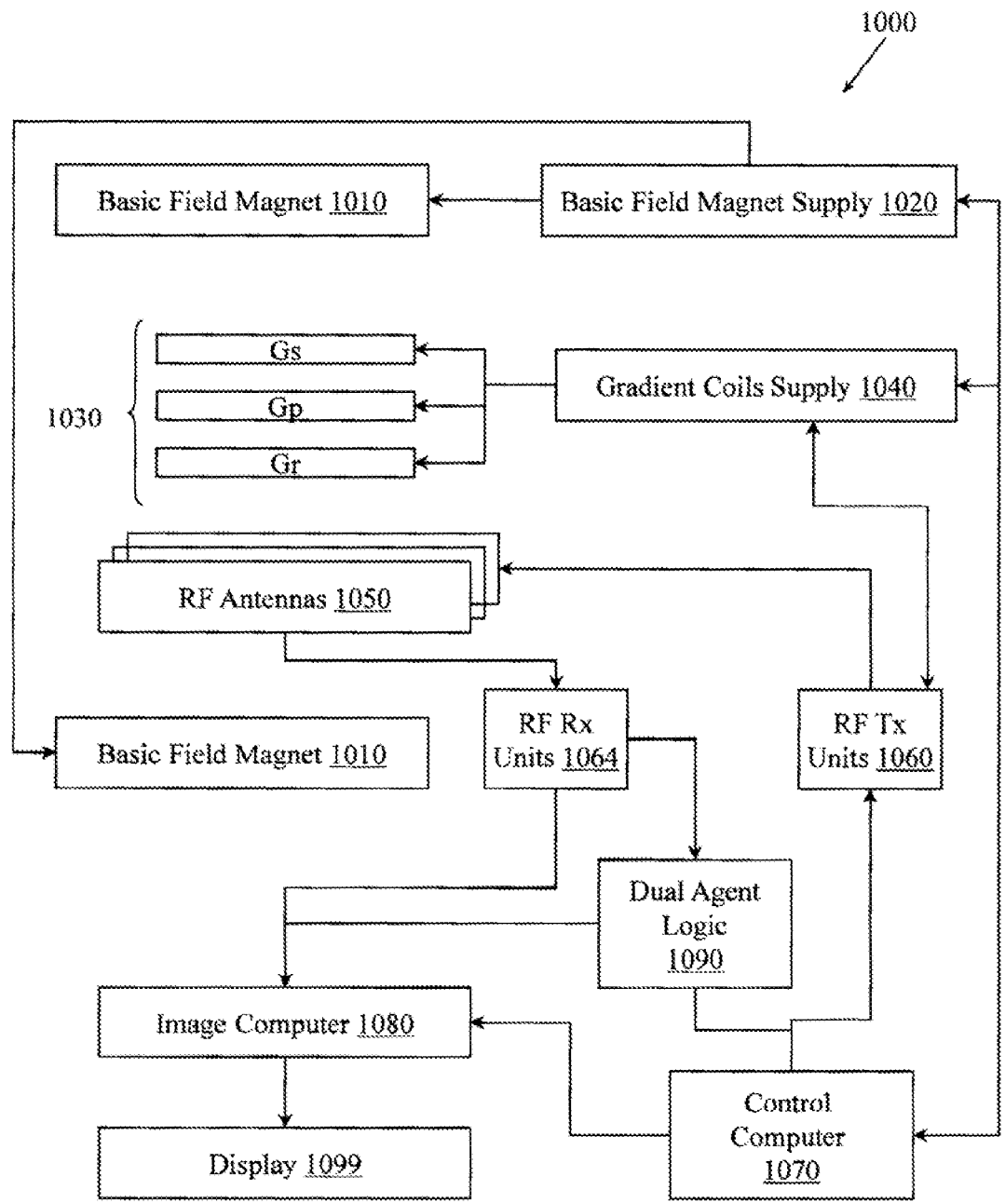
FIG. 10 illustrates an MRI apparatus configured to operate with a dual agent logic.

FIG. 10 illustrates an example MRI apparatus 1000 configured with a dual agent logic 1090. The apparatus 1000 includes a basic field magnet(s) 1010 and a basic field magnet supply 1020. Ideally, the basic field magnets 1010 would produce a uniform B$_o$ field. However, in practice, the B$_o$ field may not be uniform, and may vary over an object being imaged by the MRI apparatus 1000. MRI apparatus 1000 may include gradient coils 1030 configured to emit gradient magnetic fields like G$_S$, G$_P$ and G$_R$. The gradient coils 1030 may be controlled, at least in part, by a gradient coils supply 1040. In some examples, the timing, strength, and orientation of the gradient magnetic fields may be controlled, and thus selectively adapted, during an MRI procedure.

MRI apparatus 1000 may include a set of RF antennas 1050 that are configured to generate RF pulses and to receive resulting MR signals from an object to which the RF pulses are directed. In some examples, how the pulses are generated and how the resulting MR signals are received may be controlled, and thus may be selectively adapted, during an MRI procedure. Separate RF transmission and reception-coils can be employed. The RF antennas 1050 may be controlled, at least in part, by a set of RF transmission units 1060.

The gradient coils supply 1040 and the RF transmission units 1060 may be controlled, at least in part, by a control computer 1070. In one example, the control computer 1070 may be programmed to perform methods like those described herein. The MR signals received from the RF antennas 1050 can be employed to generate an image, and thus may be subject to a transformation process like a two dimensional FFT that generates pixilated image data. The transformation can be performed by an image computer 1080 or other similar processing device. The image data may then be shown on a display 1099. While FIG. 10 illustrates an example MRI apparatus 1000 that includes various components connected in various ways, it is to be appreciated that other MRI apparatus, NMR apparatus, or MR apparatus may include other components connected in other ways.

Dual agent logic 1090 may provide means for separating an effect of non-specific uptake of a molecular imaging agent in a sample from the effect of specific uptake of the molecular imaging agent in the sample using a quantitative relaxometry approach. In one example, separating the effects may include subtracting one signal (e.g., concentration due to non-specific uptake) from another signal (e.g., concentration due to specific uptake). While subtraction is described, other mathematical transformations may be employed to separate the effects. Dual agent logic 1090 may also provide means for providing a signal as a function of the specific uptake of the molecular imaging agent in the sample. The signal may be, for example, a visual signal, an audible signal, an electrical signal, a computer interrupt, a procedure call, a voltage on a line, a frequency on a line, or other signal.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2*d*. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

To the extent that the term "includes" or "including" is employed in the detailed description or the claims, it is intended to be inclusive in a manner similar to the term "comprising" as that term is interpreted when employed as a transitional word in a claim.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. A method, comprising:
acquiring a baseline value for a magnetic resonance (MR) parameter from a region in a sample while the sample is not exposed to a molecular imaging agent that affects the MR parameter in the sample;
acquiring a non-specific uptake value for the MR parameter while the sample is influenced by a non-specific molecular imaging agent that does not recognize a target material and where the non-specific molecular imaging agent may affect the MR parameter due to non-specific uptake of the non-specific molecular imaging agent;
acquiring a specific uptake value for the MR parameter while the sample is influenced by a specific molecular imaging agent that does recognize the target material and where the specific molecular imaging agent may affect the MR parameter due to non-specific uptake of the specific molecular imaging agent and due to specific uptake of the specific molecular imaging agent, and characterizing the region as a function of the baseline value, the non-specific uptake value, and the specific uptake value,
where the baseline value, the non-specific uptake value, and the specific uptake value are a function of magnetic resonance experienced in the sample as excited by an NMR apparatus,
where non-specific uptake of the non-specific molecular imaging agent in an area that does not include the target material and non-specific uptake of the specific molecular imaging agent in an area that does not include target material do not produce a measurably different effect on the MR parameter,
where specific uptake of the specific molecular imaging agent in an area that includes the target material and non-specific uptake of the non-specific molecular imaging agent in an area that does include the target material produce a measurably different effect on the MR parameter in the region, and
where specific uptake of the specific molecular imaging agent in an area that includes the target material and non-specific uptake of the specific molecular imaging agent in an area that does not include the target material produce a measurably different effect on the MR parameter in the region.

2. The method of claim 1, where the MR parameter is T1 relaxation or T2 relaxation.

3. The method of claim 1, where the region is bounded by a voxel used in magnetic resonance imaging (MRI) reconstruction, and where the voxel size is less than 2×2×2 mm³.

4. The method of claim 1, where the region is bounded by a voxel used in magnetic resonance imaging (MRI) reconstruction, and where the voxel size is greater than or equal to 2×2×2 mm³.

5. The method of claim 1, where the sample is excited by and where the baseline value, the non-specific uptake value, and the specific uptake value are acquired in response to a Drive Equilibrium Single Pulse Observation of T1 (DESPOT1) MR approach or a Magnetic Resonance Fingerprinting (MRF) approach.

6. The method of claim 1, where the sample is a human tissue.

7. The method of claim 1, where the target material is a protein associated with a disease.

8. The method of claim 1, where the target material is a protein associated with cancer.

9. The method of claim 1, where the target material is a protein tyrosine phosphatase µ associated with glioblastoma multiforme.

10. The method of claim 1, where the specific molecular imaging agent recognizes the target material by binding to the target material in a protein:protein interaction.

11. The method of claim 6, where the specific molecular imaging agent is a first peptide conjugated to a contrast agent.

12. The method of claim 11, where the first peptide is SBK2.

13. The method of claim 12, where the non-specific molecular imaging agent is the contrast agent, a material that changes T1 in the sample, a molecule containing Gadolinium, a second peptide conjugated to the contrast agent, or the second peptide conjugated to a molecule containing Gadolinium.

14. The method of claim 13, where the second peptide is a randomized version of the first peptide or a scrambled version of the first peptide.

15. The method of claim 1, where the baseline value is acquired before both the non-specific uptake value and the specific uptake value, and where the non-specific uptake value is acquired before the specific uptake value.

16. The method of claim 15, comprising acquiring the non-specific uptake value after the non-specific molecular imaging agent has been applied to the sample and after an effect on the MR parameter associated with the non-specific molecular imaging agent has reached a first threshold level.

17. The method of claim 16, comprising acquiring the specific uptake value after an effect on the MR parameter associated with the non-specific molecular imaging agent has fallen below the first threshold level, after the specific molecular imaging agent has been applied, and after an effect on the MR parameter associated with the specific molecular imaging agent has reached a second threshold level.

18. The method of claim 1, comprising:
reconstructing a magnetic resonance image from magnetic resonance signals received from the sample, where the magnetic resonance image includes information that is a function of the baseline value, the non-specific uptake value, or the specific uptake value.

19. The method of claim 1, where the non-specific uptake value is a function of the concentration of the non-specific molecular imaging agent in the region and where the specific uptake value is a function of the concentration of the specific molecular imaging agent in the region.

20. The method of claim 1, comprising:
controlling a signal detection apparatus to generate a signal that indicates that the target material is present in the sample.

21. The method of claim 20, where the signal identifies a phenotype of the target material.

22. The method of claim 1, the method being configured to detect a tumor that is less than 100% the size of the region.

23. The method of claim 1, where the baseline value, the non-specific uptake value, or the specific uptake value are acquired using a handheld magnetic resonance detector.

24. The method of claim 1, where characterizing the region as a function of the baseline value, the non-specific uptake value, and the specific uptake value is based, at least in part, on magnetic resonance fingerprinting.

25. An apparatus for use with a magnetic resonance (MR) apparatus, comprising:
a processor;
a memory;
a set of logics; and
an interface to connect the processor, the memory, and the set of logics, the set of logics comprising:
a first logic configured to measure a baseline T1 in a sample when no T1 altering molecular imaging agent is present in the sample;
a second logic configured to measure a change in T1 in the sample from the baseline T1 due to the presence of a non-specific molecular imaging agent in the sample;
a third logic configured to measure a change in T1 in the sample from the baseline T1 due to the presence of a specific molecular imaging agent in the sample; and
a fourth logic configured to generate a signal upon identifying that a target material is present in the sample, where the identifying is performed as a function of the baseline T1, the change in T1 due to the non-specific molecular imaging agent, and the change in T1 due to the specific molecular imaging agent,
where non-specific uptake of the non-specific molecular imaging agent in an area that does not include the target material and non-specific uptake of the specific molecular imaging agent in an area that does not include target material do not produce a measurably different effect on the MR parameter,
where specific uptake of the specific molecular imaging agent in an area that includes the target material and non-specific uptake of the non-specific molecular imaging agent in an area that does include the target material produce a measurably different effect on the MR parameter in the region, and
where specific uptake of the specific molecular imaging agent in an area that includes the target material and non-specific uptake of the specific molecular imaging agent in an area that does not include the target material produce a measurably different effect on the MR parameter in the region.

26. The apparatus of claim 25, where the specific molecular imaging agent is SBK2 conjugated to Tris-(Gd-DOTA)$_3$ and where the non-specific molecular imaging agent is a scrambled version of SBK2 conjugated to Tris-(Gd-DOTA)$_3$.

27. The apparatus of claim 25, the fourth logic being configured to generate the signal upon determining that the target material occupies less than one hundred percent of the voxel.

28. The apparatus of claim 25, the apparatus being a handheld detector.

29. The apparatus of claim 25, the apparatus being smaller than 5 cm×5 cm×5 cm.

30. The apparatus of claim 25, comprising a fifth logic configured to control when the non-specific molecular imaging agent is applied to the sample and to control when the specific molecular imaging agent is applied to the sample.

31. The apparatus of claim 25, the fifth logic being configured to:
determine a time for measuring the baseline T1;
determine a time for introducing the non-specific molecular imaging agent into the sample;
determine a time for measuring the change in T1 due to the non-specific molecular imaging agent;
determine a time for introducing the specific molecular imaging agent into the sample; and
determine a time for measuring the change in T1 due to the specific molecular imaging agent.

32. The apparatus of claim 25, where the first logic is configured to measure the baseline T1 based, at least in part on magnetic resonance fingerprinting, where the second logic is configured to measure a change in T1 in the sample based, at least in part on magnetic resonance fingerprinting, or where the third logic is configured to measure a change in T1 in the sample based, at least in part, on magnetic resonance fingerprinting.

33. An apparatus for use with a magnetic resonance apparatus, comprising:
means for separating an effect of non-specific uptake of a molecular imaging agent in a sample from the effect of specific uptake of the molecular imaging agent in the sample using a quantitative relaxometry approach; and
means for providing a signal as a function of the specific uptake of the molecular imaging agent in the sample, where the molecular imaging agent is conjugated to a magnetic resonance contrast agent.

* * * * *